(12) United States Patent
Gimbel et al.

(10) Patent No.: US 10,232,045 B2
(45) Date of Patent: Mar. 19, 2019

(54) EASY TO SWALLOW COATINGS AND SUBSTRATES COATED THEREWITH

(71) Applicant: BPSI Holdings, LLC, Wilmington, DE (US)

(72) Inventors: Jeffrey R. Gimbel, Eagleville, PA (US); Daniel To, Maple Glen, PA (US); Jason Teckoe, Dartford (GB)

(73) Assignee: BPSI HOLDINGS LLC, Wilmington, DE (US)

( * ) Notice: Subject to any disclaimer, the term of this patent is extended or adjusted under 35 U.S.C. 154(b) by 6 days.

(21) Appl. No.: 15/660,250

(22) Filed: Jul. 26, 2017

(65) Prior Publication Data

US 2018/0036413 A1    Feb. 8, 2018

Related U.S. Application Data

(60) Provisional application No. 62/370,944, filed on Aug. 4, 2016.

(51) Int. Cl.

| | | |
|---|---|---|
| *A61K 47/36* | (2006.01) | |
| *A61K 9/00* | (2006.01) | |
| *A61K 9/10* | (2006.01) | |
| *A61K 9/28* | (2006.01) | |
| *A61K 47/38* | (2006.01) | |
| *A61K 47/44* | (2017.01) | |

(52) U.S. Cl.
CPC ............ *A61K 47/36* (2013.01); *A61K 9/0053* (2013.01); *A61K 9/10* (2013.01); *A61K 9/282* (2013.01); *A61K 9/284* (2013.01); *A61K 9/286* (2013.01); *A61K 9/2853* (2013.01); *A61K 9/2866* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | |
|---|---|---|
| 4,543,370 A | 9/1985 | Porter et al. |
| 5,114,720 A | 5/1992 | Littell et al. |
| 5,470,581 A | 11/1995 | Grillo et al. |
| 9,603,805 B2 * | 3/2017 | Kudou ................ A61K 9/2072 |
| 2008/0033163 A1 | 2/2008 | Krishnamurthy et al. |
| 2012/0207831 A1 | 8/2012 | Stella et al. |
| 2013/0064889 A1 * | 3/2013 | Nutalapati ............. A61K 9/209 |
| | | 424/465 |

FOREIGN PATENT DOCUMENTS

| | | | |
|---|---|---|---|
| JP | 2017-19794 A | 1/2017 | |
| WO | WO-9115548 A1 * | 10/1991 | ............... A01C 1/06 |
| WO | 2001026633 A1 | 4/2001 | |
| WO | 2010059530 A1 | 5/2010 | |
| WO | 2012024360 A2 | 2/2012 | |

OTHER PUBLICATIONS

Star-Dri 10 Maltodextrin specification sheet, accessed online Sep. 27, 2018 (Year: 2018).*
International Search Report & Written Opinion for International Application No. PCT/US2017/043923 (dated Oct. 5, 2017).

* cited by examiner

*Primary Examiner* — Robert A Wax
*Assistant Examiner* — Melissa S Mercier
(74) *Attorney, Agent, or Firm* — Lucas & Mercanti, LLP

(57) ABSTRACT

The present invention is directed to film coating compositions for use on oral dosage forms such as compressed tablets and other orally-ingestible substrates which contain a water-soluble polymer and guar gum. The film coating compositions can be applied either directly to a substrate or after the substrate has been coated with a subcoat. In preferred aspects, the water-soluble polymer is a cellulosic or vinyl polymer. Aqueous suspensions containing the inventive film coating compositions and the coated substrates themselves are also disclosed. The resulting coated substrates have relatively low coefficients of static and dynamic friction on wet surfaces rendering them easier to swallow than prior art compositions.

24 Claims, No Drawings

EASY TO SWALLOW COATINGS AND SUBSTRATES COATED THEREWITH

1. CROSS-REFERENCE TO RELATED APPLICATIONS

This application claims the benefit of priority from U.S. Provisional Application No. 62/370,944, filed Aug. 4, 2016, the contents of which are incorporated herein by reference.

2. FIELD OF THE INVENTION

The present invention relates to film coating formulations that, when coated onto orally ingestible substrates, allow such coated substrates to be much more slippery when wet and therefore more readily swallowed versus an uncoated tablet or tablets coated with prior art coatings. The invention also relates to pharmaceutical and nutritional substrates having such film coatings and methods of preparing the same.

3. DESCRIPTION OF THE PRIOR ART

Film coatings for orally ingestible substrates are recognized for imparting many benefits to the resulting coated pharmaceutical and nutritional dosage forms. These benefits include imparting color for brand identification and reduction of medication errors as well as improving stability of the dosage forms by providing a barrier from water vapor and oxygen. It is also generally desirable that said coatings at least maintain the swallowability of dosage forms versus uncoated dosage forms, particularly for larger tablets and capsules. However, improvement in the swallowability of dosage forms is still an incompletely met need in the industry, especially for larger dosage forms and patient populations that have difficulties when swallowing (e.g. geriatric and pediatric populations).

4. SUMMARY OF THE INVENTION

It has been surprisingly found that film coating formulations comprising a water-soluble polymer and an amount of guar gum which is sufficient to reduce static friction or dynamic friction or both (as a slip aid) forms aqueous dispersions with processible viscosities and, when coated onto orally ingestible substrates, result in coated substrates with relatively low levels of static and dynamic friction when wet, i.e. after ingestion. Use of the inventive film coatings results in coated substrates that are easier to swallow, by virtue of the relatively low levels of static and dynamic friction, when compared to coated substrates of the prior art.

The present invention also relates to fully-formulated film coating systems comprising a water-soluble polymer and guar gum. The invention further relates to aqueous dispersions comprising a water-soluble polymer and guar gum, methods of preparing the same by dispersing the film coating materials (system) in ambient temperature water, orally ingestible substrates film coated with the coatings described herein, i.e. comprising a water-soluble polymer and guar gum, as well as methods of coating the substrates with the aqueous dispersions.

In one aspect of the invention, there are provided dry powder film coating compositions for the pharmaceutical, nutritional and related arts. The dry powder film coating compositions include a water-soluble polymer, guar gum and optionally plasticizers, glidants, pigments and other additives commonly used in film coating formulations. In some embodiments, maltodextrin may be beneficially added to the compositions to reduce viscosity of the aqueous dispersions and/or increase gloss of the coated orally ingestible substrates. In preferred aspects of this invention, the guar gum levels are advantageously maintained in the range of about 3-25% or preferably about 4-20%. The friction of the coated tablets is reduced as the guar gum level is increased in the dry film coating formulation; however, increasing the guar gum concentration above about 25% by weight results in aqueous dispersions that are too viscous to be used productively to coat orally ingestible substrates in many cases.

In another aspect of the invention, there are provided aqueous dispersions of the film coating compositions described above that are prepared in water which is preferably at ambient temperature. The dispersions preferably contain from about 5 to about 30% non-water ingredients content. Still further aspects include the coated substrates prepared by applying the aqueous dispersions as film coatings onto substrates, e.g. oral solid dosage forms, optionally having a subcoat thereon until the desired film coating thickness or weight gain is achieved. Such coated substrates may include one or more active pharmaceutical ingredients (APIs), and these APIs may be released in the gastrointestinal tract either immediately or over an extended period of time depending on the characteristics of the overall formulation.

In preferred aspects of this invention, film coatings are prepared that, when coated onto orally-ingestible substrates, have coefficients of static and dynamic friction of less than 3 and 1.5, respectively, when wet. The inventive film coatings are also a part of another aspect of the invention wherein methods of reducing the coefficients of static and dynamic friction of substrates, preferably oral tablets, are provided. Furthermore, the aqueous dispersions prepared from the dry powder film coating compositions of this invention have viscosities of no more than about 450 centipoise. The coated ingestible substrates have an elegant appearance with relatively high gloss and are free from cracks, pick marks and other surface defects. This combination of properties for a coating system is clearly advantageous over the prior art and existing marketed products.

5. DETAILED DESCRIPTION OF THE INVENTION

For purposes of the present invention, the following terms are given further clarification as to their meanings:

"orally-ingestible substrate" shall be understood to mean any pharmaceutically acceptable dosage form, e.g. tablet, capsule, caplet, etc. or any other veterinary, nutritional or confectionary product intended to be swallowed;

"dry powder" shall be understood to mean powders which are relatively dry to the touch rather than powders which are essentially without liquid content;

"ambient temperature" shall be understood to mean temperatures generally in the range of from about 20° C. (68° F.) to about 30° C. (86° F.)+/−3° C.;

"glycerin" is synonymous with "glycerol", and "glycerol esters" is synonymous with glycerides; and "about" when used to modify any numerical value shall be understood to include values which may vary by about +1-10%.

The inventive film coating compositions comprise a water-soluble polymer, guar gum and optionally maltodextrin, glidants, pigments, surfactants or other film coating auxiliaries. In accordance with this primary aspect of the invention, there are provided film coating composition in powder form which contain a water-soluble polymer; and guar gum. The guar gum preferably has a minimum viscosity of about 700 centipoise when dissolved in water at a 1% w/w concentration for 2 hours as measured on a Brookfield RVT viscometer at 25° C. The amount of guar gum included in the dry film coating compositions is an amount sufficient to provide a substrate, e.g. tablet, coated with an aqueous dispersion containing the film coating composition to a weight gain of at least about 0.25% by weight to impart one or more of the beneficial properties of a coefficient of static friction of less than about 3; or a coefficient of dynamic friction of less than about 1.5.

The water-soluble polymer may be any of the water-soluble polymers used in the film coating arts. These may include water-soluble cellulosic polymers, vinyl polymers or combinations thereof. The water-soluble cellulosic polymers may include hypromellose (hydroxypropyl methylcellulose), hydroxyethyl cellulose, hydroxypropyl cellulose and sodium carboxymethyl cellulose. Preferred grades of hypromellose are lower viscosity grades such as those with aqueous solution viscosities of 1, 3, 5, 6, 15 or 50 centipoise when dissolved at 2% weight/volume in water. The water-soluble vinyl polymers may include polymers derived from vinyl monomers with varying substitution and molecular weights. The water-soluble vinyl polymers may be homopolymers (i.e. made from one type of vinyl monomer) or copolymers (i.e. made from one or more vinyl monomers and potentially other types of monomers). Preferred water-soluble vinyl polymers include polyvinyl alcohol, polyvinyl alcohol-polyethylene glycol graft copolymer (e.g. Kollicoat IR) and vinylpyrrolidone-vinyl acetate copolymer 6:4 (e.g. Kollidon VA-64). Preferably, the water-soluble polymers are of sufficiently small particle size, preferably less than 250 microns, to facilitate dissolution into ambient water when forming the aqueous coating solutions. Two or more of these polymers may be used together.

In most embodiments, the amount of water-soluble polymer included in the powder mixtures of the present invention is from about 5 to about 35% by weight. In some preferred embodiments, it ranges from about 10 to about 20%. When two or more water-soluble polymers are used together, the combined total of the polymers is from about 5 to about 35% by weight, preferably from about 10 to about 30%.

When included in sufficient amounts, the guar gum imparts enhanced slip to the powder mixtures of the present invention when coated onto orally ingestible substrates as part of a film coating. While the tablets or other substrates having the film coatings of the present invention applied thereon have the expected physical properties of a film coated product in the dry state, tablets having the inventive film coatings demonstrate a significant reduction in static and/or dynamic friction values, when wet, as compared to tablets coated with prior art film coatings. Thus, after ingestion, such coated tablets demonstrate enhanced swallowability.

Guar gum may be any of the grades commonly used in pharmaceutical and nutritional products and the like. Higher viscosity grades of guar gum are preferred, e.g. those with a minimum viscosity of about 700 centipoise when dissolved in water at a 1% w/w concentration for two hours when measured on a Brookfield RVT viscometer at 25° C. and 20 rpm. Alternatively, preferred higher viscosity guar gum grades have a minimum viscosity of about 180 centipoise when dissolved in water at a 1% w/w concentration and measured on a TA Instruments Rheometer ARG2 at 25° C. and at a shear rate of 80/second. In most embodiments, the amount of guar gum included in the powder mixtures of the present invention is an amount which is sufficient to reduce at least one of the static friction, dynamic friction or both, when compared to oral substrates lacking the inventive coatings. In some aspects of the invention, the improvements are in the range of at least about 10% and more preferably at least about 20%. In further embodiments, the amount of guar gum is an amount to provide oral substrates coated the inventive film coatings with at least one of a coefficient of static friction of less than about 3 and/or a coefficient of dynamic friction of less than about 1.5; as such values are indicative of enhanced slip/swallowability.

In view of the foregoing, the amount of guar gum included in the dry powder composition in many aspects of the invention is from about 3 to about 25% by weight. In some preferred embodiments, the amount of guar gum ranges from about 4 to about 20%. The friction of the coated tablets is reduced as the guar gum level is increased in the dry film coating formulation. However, increasing the guar gum concentration above about 25% by weight can result in aqueous dispersions that are too viscous to be used productively to coat orally ingestible substrates in most cases.

It will be appreciated that the viscosity of the aqueous dispersions also depends on the concentration of the film coating formulation in water. Viscosity increases with increasing concentrations of the film coating in the aqueous dispersion. It is preferred that the concentration of film coatings in the aqueous dispersions be as high as possible while still being pumpable and sprayable to reduce the coating time required and increase productivity. The viscosity of the aqueous dispersions will increase both as the guar gum concentration in the film coating and film coating concentration in the aqueous dispersion increase. Therefore, the film coating concentration in the aqueous dispersions must be determined based on the guar gum concentration in the film coating. If higher guar gum concentrations, i.e. amounts of more than 20% guar gum, based upon the weight of the dry powder ingredients, are used in the film coating dispersion, lower concentrations of the film coating composition, i.e. from about 5 to about 15%, in the aqueous dispersion are preferable such that the viscosity of the aqueous dispersion is less than about 450 centipoise (cP). If lower guar gum concentrations, i.e. less than 10%, are used in the film coating composition, higher concentrations of the film coating, i.e. from about 15 to about 25%, in the aqueous dispersions are preferred to minimize coating time and maximize productivity.

Aqueous dispersion viscosity is also dependent on the nature of the polymer used in the film coating formulation. When used in film coating formulations at equivalent concentrations, cellulosic polymers often impart a higher solution viscosity than vinyl polymers do. Therefore, higher guar gum concentrations may be used in film coating formulations with vinyl polymers than with cellulosic polymers in many cases. See Table below:

| Polymer Type | Preferred Guar Gum Range (wt. %) |
| --- | --- |
| cellulosic polymers | About 3-8 |
| vinyl polymers | About 6-20 |

Therefore, in certain embodiments, it will be preferred to use guar gum in combination with vinyl polymers such that the guar gum concentration may be maximized and, correspondingly, the friction of coated tablets be minimized, while still allowing the concentration of the film coating in aqueous dispersion to be sufficiently high, while maintaining processible viscosity, so that the coating process will be efficient. Both cellulosic polymers and vinyl polymers may be used in the same formulation, and it will be appreciated from the foregoing that the amount of guar gum should vary depending on the ratio of cellulosic to vinyl polymers to ensure that the viscosity of the resulting aqueous dispersion, i.e. containing the film coating composition, is less than about 450 centipoise. Therefore, when using combinations of cellulosic and vinyl polymers, the preferred guar gum concentrations are in the range of 3-20%, depending on the ratio of the cellulosic and vinyl polymers.

Maltodextrin is optionally used to reduce viscosity of the aqueous dispersions and/or increase gloss of the coated orally ingestible tablets. The maltodextrin may be any of the grades commonly used in pharmaceutical and nutritional products and the like. Maltodextrins having a dextrose equivalent (DE) of <20 are preferred. Maltodextrins having a DE of 11-14 are particularly preferred. The dextrose equivalent value is a measure of the extent of starch-polymer hydrolysis and, correspondingly, the amount of reducing sugars present in a sugar product, relative to dextrose (a.k.a. glucose), expressed as a percentage on a dry basis. For example, a maltodextrin with a DE of 10 would have 10% of the reducing power of dextrose (which has a DE of 100). In most embodiments, the amount of maltodextrin, when included in the powder mixtures of the present invention is from about 0.1 to about 80% by weight. For formulations without added colorants (i.e. clear formulations), the preferred amount of maltodextrin in the powder mixtures is about from 50 to about 80%. For formulations with added pigments, the preferred amount of maltodextrin in the powder mixtures is from about 5 to about 60%.

A glidant is optionally used to help tablets flow over each other and so generate a smooth surface finish. A preferred glidant is talc. The amount of glidant, when present, will depend upon need, but can broadly range from 0.1 to about 30% in the powder mixtures. Preferably, the range is from about 10 to about 20%.

A plasticizer is optionally used to help to aid in film formation. Preferred plasticizers are those that are known to plasticize water-soluble cellulosic polymers or vinyl polymers and may include polyethylene glycol, glycerin, triacetin, medium chain triglycerides and medium chain mono/diglycerides. Medium chain triglycerides are preferred. The amount of plasticizer, when present, will depend upon need, but can broadly range from about 1 to about 10% by weight in the powder mixtures. Preferably, the range is from about 2.5 to about 10%.

Pigments are also optionally added and may be any food or pharmaceutically approved colors, opacifiers or dyes. For example, the pigments may be aluminum lakes, iron oxides, titanium dioxide, natural colors or pearlescent pigments (e.g. mica based pigments sold under the Candurin trade name). Examples of such pigments are listed in U.S. Pat. No. 4,543,570, the contents of which are incorporated herein by reference. When included, the pigments may be used in the powder mixtures in a range (by weight) from about greater than 0 to about 40% pigment, preferably, from about 4 to about 32% and, more preferably, from about 7 to about 30%. It will be understood, however, that the amount of pigment employed in the powder mixtures of the invention is an amount which is sufficient or effective to impart the required appearance of the outer coating to the surface of the substrate to be coated.

Furthermore, the powder mixtures may also include supplemental or auxiliary ingredients typically found in film coatings. A non-limiting list of such adjuvants includes surfactants, suspension aids, sweeteners, flavorants, etc. and mixtures thereof.

The powder mixtures are prepared using standard dry blending or mixing techniques known to those of ordinary skill. For example, the ingredients are individually weighed, added to a suitable apparatus and blended for a sufficient time until a substantially uniform mixture of the ingredients is obtained. The time required to achieve such substantial uniformity will, of course, depend upon the batch size and apparatus used. Addition of liquid plasticizers such as the medium chain triglycerides and medium chain mono/diglycerides will occur such that no significant agglomeration or separation will occur. This can be accomplished by gradually adding the liquid to the dry ingredients while blending. A preblend may also be utilized, wherein the liquid plasticizers are first added to a portion of the dry ingredients and then the remaining dry material is added. The preblend may be prepared in bulk and used as needed to reduce the mixing time required for smaller batches. In all cases, when the liquid plasticizers are added to the dry ingredients, the components must be mixed for a time sufficient to ensure homogeneity.

As mentioned above, batch sizes will vary upon need. A non-limiting list of suitable blending devices include diffusion blenders such as a cross flow, V-blender, or hub blender, available from Patterson-Kelly, or convection blenders, such as Ruberg or CVM blenders, available from Azo, Servolift and Readco, respectively, may be used. Blending of the aforementioned formulations may also be achieved by processing ingredients into a granular form to produce a non-dusting granular coating composition by methods including, but not limited to, wet massing, fluid bed granulation, spray granulation and dry compaction, roller compaction or slugging. Other manners of blending will be apparent to those of ordinary skill.

Some preferred dry film coating compositions in accordance with the present invention include:

| Ingredient | % by weight About | Preferred About |
|---|---|---|
| Water-soluble polymer(s) | 5-35 | 10-20 |
| Guar gum | 3-25 | 4-20 |
| Maltodextrin | 0-80 | 5-60 (pigmented formulations) 50-80 (unpigmented formulations) |
| Glidant | 0-30 | 10-20 |
| Plasticizer | 0-10 | 2.5-10 |
| Pigments | 0-40 | 4-32 |
| Optional or aux. ingredients | 0-20 | — |

It will be understood from the foregoing table that the preferred dry film coating compositions will include at least a water-soluble polymer and guar gum as described herein. The additional ingredients, if included, will cause the amount of water-soluble polymer and guar gum to be reduced proportionally, but both components will still be within the ranges described herein, so that the total amount of all ingredients in the dry blend will be 100% by weight.

For purposes of illustration and not limitation, an aqueous dispersion having about 20% non-water ingredients can be formed by dispersing 100 parts of a blended powder mixture described hereinabove into 400 parts of ambient temperature water. The water is weighed into a suitable vessel, i.e. one with a diameter approximately equal to the depth of the final suspension. A low shear mixer, preferably one having a mixing blade with a diameter about one third the diameter of the mixing vessel, is lowered into the water and turned on to create a vortex from the edge of the vessel down to about just above the mixing blade to prevent entrapment of air. The 100 parts of dry film coating composition is added to the vortex at a rate where there is no excessive buildup of dry powder. The speed and depth of the mixing blade is adjusted to avoid air being drawn into the suspension so as to avoid foaming. The suspension is stirred at low speed, preferably 350 rpm or less, for a time sufficient to ensure that a homogeneous mixture is formed. Using the above batch size as a guide, about 45 minutes mixing time is required. The suspension is then ready for spraying onto pharmaceutical substrates and the like. Those of ordinary skill will also realize that there are many ways of preparing a substantially homogenous mixture of the solids in water and that the scope of the invention is in no way dependent on the apparatus used. It is contemplated that suitable aqueous dispersions will contain from about 5 to about 30% and preferably from about 10 to about 20% non-water ingredients therein.

In still further embodiments of the invention, there are provided orally-ingestible substrates coated with the inventive film coating formulations. The coated substrates have relatively low coefficients of static and dynamic friction as well as elegant appearance—i.e. relatively high gloss and logos free of particulate matter.

As will be described in the examples below, the methods include applying the film coating compositions as aqueous suspensions to the surfaces of orally ingestible substrates. The film coating can be applied as part of a pan coating or spray coating process commonly used to coat such articles. The amount of coating applied will depend upon several factors, including the nature and functionality of the film coating, the substrate to be coated and the apparatus employed to apply the coating, etc. In some immediate release applications of the invention, the substrates will be tablets and will be coated to a theoretical weight gain of from about 0.25 to about 5.0%. Preferably, the theoretical weight gain is from about 1.0 to about 4.5% and more preferably, the theoretical weight gain is from about 2.0 to about 4.0% by weight of said substrate. As mentioned above, the coating solutions of the present invention may also include auxiliary ingredients in addition to the powder mixture and the water. For purposes of the present invention, it will be understood that "theoretical weight gain" and "weight gain" are used interchangeably with respect to indicating the amount of film coating applied to a substrate. The practice of the industry is to weight a fixed quantity of substrates or tablets in coating pan, apply the film coating dispersion to the substrates until the desired weight gain for the entire batch is achieved, i.e, 0.5%, The resulting substrates are individually accepted as having a weight gain of 0.5% without measuring each substrate. Such measurements for determining the amount of film coating applied to a substrate is accepted as the theoretical weight gain for each substrate and the batch.

The coated, orally-ingestible substrates described above can also include a subcoat film coating between the orally-ingestible substrate and the inventive film coating. The subcoat selected is preferably based on an edible film coating composition that is compatible with and adheres to both the orally-ingestible substrate and the inventive coating. Thus, the artisan may choose from a wide variety of pharmaceutical or food-acceptable coatings for use as subcoats in the present invention. The subcoat is also applied to the substrate to provide from about a 0.25 to about a 5.0% weight gain to the orally-ingestible substrate.

Regardless of the method employed or the specific materials included in the film coating compositions, the orally-ingestible substrates of the present invention will include a film coating which contains a water-soluble polymer and a sufficient amount of guar gum to reduce at least one of the static friction, dynamic friction or both, preferably by at least about 10% when compared to oral substrates lacking the inventive coatings.

In another aspect of the invention, there are provided methods of reducing the coefficient of static and/or dynamic friction of an orally ingestible substrate, e.g. compressed tablet. The methods include coating a substrate with an aqueous dispersion containing a water-soluble polymer and a slip enhancing amount of guar gum until the amount of film coating dried thereon is an amount sufficient to reduce at least one of the static friction, dynamic friction or both of the substrate. Stated alternatively, the methods include applying a film coating dispersion containing water-soluble polymer and guar gum having a minimum viscosity of about 700 centipoise when dissolved in water at a 1% w/w concentration for 2 hours as measured on a Brookfield RVT viscometer at 25° C., the guar gum being present in an amount sufficient to provide the orally ingestible substrate coated with said aqueous dispersion to a weight gain of at least about 0.25% by weight, with a reduction of the coefficient of static friction and/or the coefficient of dynamic friction of the coated orally ingestible substrate.

In preferred aspects, film coating is applied to the substrates until the coefficient of static friction for the substrate is less than about 3 and/or until the coefficient of dynamic friction is less than about 1.5. In many embodiments, aqueous dispersions containing from about 5 to about 30% non-aqueous content, i.e. the inventive film coating compositions, are applied until a weight gain of at least about 0.25% is achieved. Preferably, the substrate weight gain caused by the application of the film coating dispersion is about 5% or less.

6. EXAMPLES

The following examples serve to provide further appreciation of the invention but are not meant in any way to restrict the effective scope of the invention. All ingredients are expressed as being by weighty %©. Unless otherwise specified, the guar gum used in the following examples produced a 1% aqueous solution with a viscosity equal to about 207 centipoise at 25° C. and at a shear rate of 80/see as measured on a TA Instruments ARG2 rheometer.

Example 1

A preferred pigmented formulation for an inventive dry coating composition is the following:

| Component | Weight % |
|---|---|
| Maltodextrin (DE = 11-14) | 36.5 |
| Talc | 15.0 |
| Hypromellose, 5 cP grade | 7.5 |
| Hypromellose, 15 cP grade | 7.5 |
| Guar gum | 6.0 |
| Medium chain triglycerides | 2.5 |

-continued

| Component | Weight % |
|---|---|
| Titanium dioxide | 20.0 |
| Blue#2 aluminum lake pigment | 5.0 |
| | 100.0 |

Preparation of the Dry Film Coating Composition:

The dry film coating composition was prepared by adding all dry ingredients (maltodextrin, talc, hypromellose, guar gum, titanium dioxide and Blue#2 aluminum lake) into a laboratory blender and blending for 5 minutes until a homogenous mixture was produced. Medium chain triglycerides, the only liquid component, was then gradually added to the dry mixture, and the total mixture was blended for an additional 2 minutes after all liquid was introduced.

Preparation of the Aqueous Dispersion:

The dry film coating composition (100 parts) was dispersed into 400 parts of ambient temperature water to make an aqueous coating suspension having 20% w/w non-water ingredients. The water was weighed into a vessel with a diameter approximately equal to the depth of the final dispersion. A low shear mixer was lowered into the water and turned on to create a vortex from the edge of the vessel down to just above the mixing blade to prevent entrapment of air. The 100 parts of dry film coating composition was added to the vortex at a rate where there was no excessive buildup of dry powder or foam. The speed and depth of the mixing blade was adjusted to avoid air being drawn into the suspension so as to avoid foaming. The suspension was stirred at low speed (350 rpm or less) for 45 minutes to form a homogeneous aqueous dispersion suitable for coating. The viscosity of the resulting aqueous dispersion was 213 centipoise (cP) at a shear rate of 80/s.

Coating of Tablets:

A mixed batch of 50 grams of 10-mm round flat-faced placebo tablets and 950 grams of 10-mm bi-convex round placebos were coated with aqueous dispersion of Example 1 at a spray rate of 8 grams/min in a Labcoat I (O'Hara Technologies Inc., Canada) outfitted with a 12" fully perforated pan. A theoretical coating weight gain of 3.0% was applied to the tablets. The resulting coated tablets were smooth, non-tacky, glossy and free from cracks or other surface defects.

Determination of Coefficients of Static and Dynamic Friction:

The wet slip behavior of each film coating system was characterized by determining the coefficients of static and dynamic friction on the flat-faced tablets. Three tablets weighted with a 0.5 N normal force were dragged across a water saturated substrate (SAS) at 500 mm/min with an Instron testing system (5542, Instron, USA). The static friction coefficient is the ratio between the force required to initiate tablet movement and the normal force. The dynamic friction coefficient is the ratio between the average force during tablet movement and the normal force. The average static and dynamic friction values (n=5) were 2.553 and 1.455, respectively.

Example 2

A preferred unpigmented (clear) formulation for an inventive dry coating composition is the following:

| Component | Weight % |
|---|---|
| Maltodextrin (DE = 11-14) | 61.5 |
| Talc | 15.0 |
| Hypromellose, 5 cP grade | 7.5 |
| Hypromellose, 15 cP grade | 7.5 |
| Guar gum | 6.0 |
| Medium chain triglycerides | 2.5 |
| | 100.0 |

Preparation of the Dry Film Coating Composition:

The dry film coating composition was prepared by adding all dry ingredients (maltodextrin, talc, hypromellose, and guar gum) into a laboratory blender and blending for 5 minutes until a homogenous mixture was produced. Medium chain triglycerides, the only liquid component, was then gradually added to the dry mixture, and the total mixture was blended for an additional 2 minutes after all liquid was introduced.

Preparation of the Aqueous Dispersion:

The dry film coating composition (40 parts) was dispersed into 360 parts of ambient temperature water to make an aqueous coating suspension having 10% w/w non-water ingredients according to the method described in Example 1. The viscosity of the resulting aqueous dispersion was 23 cP at a shear rate of 80/s.

Coating of Tablets:

A mixed batch of 50 grams of 10-mm round flat-faced placebo tablets and 950 grams of 10-mm bi-convex round placebos were coated with aqueous dispersion of Example 2 at a spray rate of 8 grams/min in a Labcoat I (O'Hara Technologies Inc., Canada) outfitted with a 12" fully perforated pan. A theoretical coating weight gain of 3.0% was applied to the tablets. The resulting coated tablets were smooth, non-tacky, glossy and free from cracks or other surface defects.

Determination of Coefficients of Static and Dynamic Friction:

The wet slip behavior of each film coating system was determined according to the method of Example 1. The average static and dynamic friction values (n=5) were 2.262 and 1.075, respectively.

Examples 3-4

Additional inventive, unpigmented formulations were prepared according to the following ratios:

| Component | Example 3 Weight % | Example 4 Weight % |
|---|---|---|
| Maltodextrin (DE = 5) | 76.0 | 74.0 |
| Sodium carboxymethylcellulose | 10.0 | 10.0 |
| Guar gum | 4.0 | 6.0 |
| Glycerol monocaprylocaprate | 10.0 | 10.0 |
| | 100.0 | 100.0 |

Comparative Example A-B

Comparative unpigmented formulations were prepared according to the following ratios:

| Component | Comparative Example A Weight % | Comparative Example B Weight % |
|---|---|---|
| Maltodextrin (DE = 5) | 79.0 | 78.0 |
| Sodium carboxymethylcellulose | 10.0 | 10.0 |
| Guar gum | 1.0 | 2.0 |
| Glycerol monocaprylocaprate | 10.0 | 10.0 |
|  | 100.0 | 100.0 |

The aqueous dispersion preparation and coating process were conducted in an analogous fashion to that described in Example 2. The average coefficients of static and dynamic friction for Examples 3-4 and Comparative Examples A-B are summarized in the following table.

| Example | Guar Gum Level (wt. %) | Coefficient of Static Friction | Coefficient of Dynamic Friction |
|---|---|---|---|
| Comparative Example A | 1 | 3.172 | 1.937 |
| Comparative Example B | 2 | 3.025 | 1.824 |
| Example 3 | 4 | 2.762 | 1.379 |
| Example 4 | 6 | 2.741 | 1.215 |

When guar gum is present at 4-6%, the coefficients of static and dynamic friction are less than 3 and 1.5, respectively, which is indicative of enhanced slip/swallowability. When guar gum levels are at the 1-2% level, the coefficients of static and dynamic friction are greater than 3 and 1.5, respectively, which is indicative of relatively poor slip/swallowability. The resulting coated tablets from Examples 3 & 4 were also smooth, non-tacky, glossy and free from cracks or other surface defects.

Comparative Example C

The following prior art formulation was prepared for comparison:

| Component | Weight % |
|---|---|
| Hydroxypropyl cellulose | 42.0 |
| Hypromellose, 6 cP grade | 42.0 |
| Titanium dioxide | 16.0 |
|  | 100.0 |

12 parts of this dry powder formulation were dispersed in 88 parts water according to the method described in Example 1. Coated tablets were prepared and frictional analyses were completed according to the methods described in Example 1 as well. The average static and dynamic friction values (n=5) were 3.454 and 1.769, respectively.

Comparative Example D

The following prior art formulation was prepared for comparison:

| Component | Weight % |
|---|---|
| Polyvinyl alcohol | 45.52 |
| Talc | 20.00 |
| Soya lecithin | 2.00 |
| Xanthan gum | 0.48 |
| Titanium dioxide | 32.00 |
|  | 100.00 |

20 parts of this dry powder formulation were dispersed in 80 parts water according to the method described in Example 1. Coated tablets were prepared and frictional analyses were completed according to the methods described in Example 1 as well. The average coefficients of static and dynamic friction values (n=5) were 3.331 and 2.793, respectively.

Thus, the prior art formulations of Comparative Examples C and D (both without guar gum) have coefficients of static and dynamic friction greater than 3 and 1.5, respectively, which is indicative of relatively poor slip/swallowability.

Examples 5-7

Film coating compositions and aqueous dispersions comprising them were prepared using polyvinyl alcohol as a water-soluble polymer by methods similar to those described in Example 1. Aqueous dispersion and coated tablet properties were similarly assessed.

| | Example | | |
|---|---|---|---|
| | 5 Wt. % | 6 Wt. % | 7 Wt. % |
| Component | | | |
| Maltodextrin | 36.5 | 32.5 | 27.5 |
| Talc | 15.0 | 15.0 | 15.0 |
| Polyvinyl alcohol | 15.0 | 15.0 | 15.0 |
| Guar gum | 6.0 | 10.0 | 15.0 |
| Medium chain triglycerides | 2.5 | 2.5 | 2.5 |
| Titanium dioxide | 25.0 | 25.0 | 25.0 |
| Totals | 100 | 100 | 100 |
| Performance | | | |
| Viscosity of aqueous dispersion at 20% solids and shear rate of 80/s in centipoise | 33 | 93 | 296 |
| Coating process performance | Pass | Pass | Pass |
| Qualitative appearance of coated tablets | Pass | Pass | Pass |
| Coefficient of static friction (coated tablets) | 2.32 | 2.22 | 2.06 |
| Coefficient of dynamic friction (coated tablets) | 1.23 | 1.05 | 0.89 |

Examples 5-7 showed that the coefficients of static and dynamic friction decreased with increasing guar gum concentration. A coating process performance of "pass" indicates that the aqueous dispersion was pumpable and that the coating was applied with no gun clogs, tablet sticking or process interruptions. A qualitative appearance of "pass" indicates that the coated tablets were smooth, non-tacky, glossy and free from cracks or other surface defects.

Examples 8-11

Film coating compositions and aqueous dispersions comprising them were prepared using polyvinyl alcohol-polyethylene glycol graft copolymer as a water-soluble polymer by methods similar to those described in Example 1. Aqueous dispersion and coated tablet properties were similarly assessed.

|  | Example | | | |
|---|---|---|---|---|
|  | 8 Wt. % | 9 Wt. % | 10 Wt. % | 11 Wt. % |
| Component | | | | |
| Maltodextrin | 36.5 | 32.5 | 27.5 | 22.5 |
| Talc | 15.0 | 15.0 | 15.0 | 15.0 |
| Polyvinyl alcohol-polyethylene glycol graft copolymer | 15.0 | 15.0 | 15.0 | 15.0 |
| Guar gum | 6.0 | 10.0 | 15.0 | 20.0 |
| Medium chain triglycerides | 2.5 | 2.5 | 2.5 | 2.5 |
| Titanium dioxide | 25.0 | 25.0 | 25.0 | 25.0 |
| Totals | 100 | 100 | 100 | 100 |
| Performance | | | | |
| Viscosity of aqueous dispersion at 20% solids and shear rate of 80/s in centipoise | 19 | 36 | 92 | 222 |
| Coating process performance | Pass | Pass | Pass | Pass |
| Qualitative appearance of coated tablets | Pass | Pass | Pass | Pass |
| Coefficient of static friction (coated tablets) | 2.18 | 2.05 | 1.93 | 1.83 |
| Coefficient of dynamic friction (coated tablets) | 1.24 | 1.17 | 1.00 | 0.95 |

Examples 8-11 again showed that the coefficients of static and dynamic friction decreased with increasing guar gum concentration. A coating process performance of "pass" indicates that the aqueous dispersion was pumpable and that the coating was applied with no gun clogs, tablet sticking or process interruptions. A qualitative appearance of "pass" indicates that the coated tablets were smooth, non-tacky, glossy and free from cracks or other surface defects.

Examples 12-15

Film coating compositions and aqueous dispersions comprising them were prepared using polyvinyl alcohol-polyethylene glycol graft copolymer as a water-soluble polymer by methods similar to those described in Example 1. Aqueous dispersion and coated tablet properties were similarly assessed.

|  | Example | | | |
|---|---|---|---|---|
|  | 12 Wt. % | 13 Wt. % | 14 Wt. % | 15 Wt. % |
| Component | | | | |
| Maltodextrin | 36.5 | 32.5 | 27.5 | 22.5 |
| Talc | 15.0 | 15.0 | 15.0 | 15.0 |
| Vinylpyrrolidone-vinyl acetate copolymer (6:4) | 15.0 | 15.0 | 15.0 | 15.0 |
| Guar gum | 6.0 | 10.0 | 15.0 | 20.0 |
| Medium chain triglycerides | 2.5 | 2.5 | 2.5 | 2.5 |
| Titanium dioxide | 25.0 | 25.0 | 25.0 | 25.0 |
| Totals | 100 | 100 | 100 | 100 |
| Peformance | | | | |
| Viscosity of aqueous dispersion at 20% solids and shear rate of 80/s in centipoise | 19 | 38 | 150 | 354 |

-continued

|  | Example | | | |
|---|---|---|---|---|
|  | 12 Wt. % | 13 Wt. % | 14 Wt. % | 15 Wt. % |
| Coating process performance | Pass | Pass | Pass | Pass |
| Qualitative appearance of coated tablets | Pass | Pass | Pass | Pass |
| Coefficient of static friction (coated tablets) | 2.11 | 2.09 | 1.97 | 1.89 |
| Coefficient of dynamic friction (coated tablets) | 1.20 | 1.13 | 1.04 | 1.00 |

Examples 12-15 once again showed that the coefficients of static and dynamic friction decreased with increasing guar gum concentration. A coating process performance of "pass" indicates that the aqueous dispersion was pumpable and that the coating was applied with no gun clogs, tablet sticking or process interruptions. A qualitative appearance of "pass" indicates that the coated tablets were smooth, non-tacky, glossy and free from cracks or other surface defects.

Examples 16-17

Film coating compositions and aqueous dispersions comprising them were prepared using hydroxyethyl cellulose and hydroxypropyl cellulose as water-soluble polymers by methods similar to those described in Example 1. Aqueous dispersion and coated tablet properties were similarly assessed.

|  | Example | |
|---|---|---|
|  | 16 Wt. % | 17 Wt. % |
| Component | | |
| Maltodextrin | 36.5 | 36.5 |
| Talc | 15.0 | 15.0 |
| Hydroxyethyl cellulose | 15.0 | |
| Hydroxypropyl cellulose | | 15.0 |
| Guar gum | 6.0 | 6.0 |
| Medium chain triglycerides | 2.5 | 2.5 |
| Titanium dioxide | 25.0 | 25.0 |
| Totals | 100 | 100 |
| Performance | | |
| Viscosity of aqueous dispersion at 20% solids and shear rate of 80/s in centipoise | 251 | 332 |
| Coating process performance | Pass | Pass |
| Qualitative appearance of coated tablets | Pass | Pass |
| Coefficient of static friction (coated tablets) | 1.86 | 2.16 |
| Coefficient of dynamic friction (coated tablets) | 0.80 | 1.06 |

Examples 16-17 showed that alternative water-soluble cellulosic polymers may be used successfully. A coating process performance of "pass" indicates that the aqueous dispersion was pumpable and that the coating was applied with no gun clogs, tablet sticking or process interruptions. A qualitative appearance of "pass" indicates that the coated tablets were smooth, non-tacky, glossy and free from cracks or other surface defects.

Examples 18-20 and Comparative Example E

Film coating compositions and aqueous dispersions comprising them were prepared using as described in Example 1. Aqueous dispersion and coated tablet properties were similarly assessed.

|  | Example | | | |
|---|---|---|---|---|
| Component | 18 Wt % | 19 Wt. % | 20 Wt % | E Wt. % |
| Maltodextrin | 63.5 | 12.0 | 9.5 | 61.5 |
| Talc | 15.0 | 20.5 | 20.5 | 15.0 |
| Hypromellose, 5 cP grade |  |  |  | 7.5 |
| Hypromellose, 6 cP grade | 5.0 | 10.0 | 10.0 |  |
| Hypromellose, 15 cP grade | 10.0 |  |  | 7.5 |
| Polyvinyl alcohol |  | 15.0 | 17.5 |  |
| Guar gum | 4.0 | 15.0 | 15.0 |  |
| Guar gum (viscosity of 1% aqueous solution = 56 cP at 25° C. and at shear rate of 80/sec) |  |  |  | 6.0 |
| Medium chain triglycerides | 2.5 | 2.5 | 2.5 | 2.5 |
| Titanium dioxide |  | 20.0 | 20.0 |  |
| Yellow #6 aluminum lake |  | 5.0 |  |  |
| Blue #2 aluminum lake |  |  | 5.0 |  |
| Totals | 100 | 100 | 100 | 100 |
| Performance |  |  |  |  |
| Viscosity of aqueous dispersion at 20% solids and shear rate of 80/s in centipoise | * | 348 | 339 | 354 |
| Coating process performance | Pass | Pass | Pass | Pass |
| Qualitative appearance of coated tablets | Pass | Pass | Pass | Fail |
| Coefficient of static friction (coated tablets) | 2.08 | 2.38 | 2.35 | 2.61 |
| Coefficient of dynamic friction (coated tablets) | 1.18 | 1.13 | 1.12 | 1.60 |

*Viscosity at 8% solids and shear rate of 80/sec was 13.5 centipoise.

Examples 18-20 showed that the coefficients of static and dynamic friction were below the desired maxima of 3 and 1.5, respectively. A coating process performance of "pass" indicates that the aqueous dispersion was pumpable and that the coating was applied with no gun clogs, tablet sticking or process interruptions. A qualitative appearance of "pass" indicates that the coated tablets were smooth, non-tacky, glossy and free from cracks or other surface defects. Comparative example E, containing a low viscosity guar gum, resulted in a coated tablet that had low gloss and was tacky and, therefore, failed the appearance test. The resulting coated tablets from comparative example E also had a coefficient of dynamic friction above the desired maximum of 1.5.

Examples 21-22

Additional film coating compositions are prepared in accordance with the present invention.

|  | Example | |
|---|---|---|
| Component | 21 Wt. % | 22 Wt. % |
| Talc | 30 | 25 |
| Hypromellose, 6 cP grade | 10 | 10 |
| Polyvinyl alcohol | 17.5 | 17.5 |
| Guar gum | 15 | 15 |
| Medium chain triglycerides | 2.5 | 2.5 |
| Titanium dioxide | 20 | 25 |
| Blue #2 aluminum lake | 5 | 5 |
| Totals | 100 | 100 |

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed in:

1. A film coating composition in powder blend form, consisting of:
a water-soluble polymer selected from the group consisting of cellulosic polymers, vinyl polymers, and mixtures thereof,
wherein the cellulosic polymers are water soluble cellulosic polymers selected from the group consisting of hypromellose (hydroxypropyl methylcellulose), hydroxyethyl cellulose, hydroxypropyl cellulose and sodium carboxymethyl cellulose and the vinyl polymers are selected from the group consisting of polyvinyl alcohol, polyvinyl alcohol-polyethylene glycol graft copolymer and vinylpyrrolidone-vinyl acetate copolymer 6:4;
guar gum;
one or more of a glidant; a plasticizer; a pigment; and maltodextrin
said guar gum having a minimum viscosity of about 700 centipoise when dissolved in water at a 1% w/w concentration for 2 hours as measured on a Brookfield RVT viscometer at 25° C., and said guar gum being present in an amount sufficient to provide a substrate coated with an aqueous dispersion containing the film coating composition to a weight gain of at least about 0.25% by weight with at least one of
a) a coefficient of static friction of less than about 3; or
b) a coefficient of dynamic friction of less than about 1.5.

2. The composition of claim 1, wherein the guar gum comprises 3-25% or 4-20% by weight of the composition.

3. The composition of claim 1, wherein the polymer is hypromellose.

4. The composition of claim 3, wherein the hypromellose has an aqueous solution viscosity of 1, 3, 5, 6, 15 or 50 centipoise when dissolved at 2% weight/volume in water.

5. A composition according to claim 1 wherein the water-soluble polymer is a cellulosic polymer and the amount of guar gum is about 3-8% by weight.

6. A composition according to claim 1 wherein the water-soluble polymer is a vinyl polymer and the amount of guar gum is about 6-20% by weight.

7. The composition of claim 1 wherein the plasticizer comprises medium chain triglycerides.

8. The composition of claim 1 wherein the maltodextrin comprises 0.1-80% by weight of the film coating composition.

9. The composition of claim 1, wherein the maltodextrin has a DE (dextrose equivalent) of less than 20.

10. The composition of claim 1, wherein the maltodextrin has a DE (dextrose equivalent) of between about 11 and about 14.

11. The composition of claim 1 wherein the water-soluble polymer comprises from about 5 to about 35% by weight, or from about 10 to about 20% by weight of the dry powder composition.

12. A composition according to claim 1, consisting of:
about 5 to about 35%/wt. water soluble polymer;
about 3 to about 25%/wt. guar gum;
up to about 80%/wt. maltodextrin;
up to about 30%/wt. glidant;
up to about 10%/wt. plasticizer;
up to about 40%/wt. pigments and up to about 20%/wt. optional or auxiliary ingredients, the total not exceeding 100%/wt. of the composition.

13. A composition according to claim 12, consisting of:
about 10 to about 20%/wt. water soluble polymer;
about 4 to about 20%/wt. guar gum;
about 5 to about 60%/wt. maltodextrin;
about 10 to about 20%/wt. glidant;
about 2.5 to about 10%/wt. plasticizer; and
about 4 to about 32%/wt. pigments,
the total not exceeding 100%/wt. of the composition.

14. A composition according to claim 12, consisting of:
about 10 to about 20%/wt. water soluble polymer;
about 4 to about 20%/wt. guar gum;
about 50 to about 80%/wt. maltodextrin;
about 10 to about 20%/wt. glidant; and
about 2.5 to about 10%/wt. plasticizer,
the total not exceeding 100%/wt. of the composition.

15. An aqueous dispersion prepared by mixing a composition according to claim 1 in water, said water optionally being at ambient temperature.

16. An aqueous dispersion, comprising a composition according to claim 1 and water.

17. An aqueous dispersion of claim 16, having a viscosity of less than about 450 centipoise.

18. An orally-ingestible substrate coated with an aqueous dispersion of claim 16.

19. The orally-ingestible substrate according to claim 18, wherein the coating is applied to a weight gain selected from the group consisting of
a) from about 0.25 to about 5%,
b) from about 1.0 to about 4.5; and
c) from about 2.0 to about 4.0.

20. A coated orally-ingestible substrate according to claim 19, having an average coefficient of static friction of less than about 3.0 and/or a coefficient of dynamic friction of less than about 1.5.

21. A method of reducing the coefficient of static and/or dynamic friction of an orally ingestible substrate, comprising:
coating an orally ingestible substrate with an aqueous dispersion containing the composition of claim 1 to a weight gain of at least about 0.25% by weight,
whereby at least one of the coefficient of static friction or the coefficient of dynamic friction of the coated orally ingestible substrate is reduced.

22. The method of claim 21, wherein the coated orally ingestible substrate has a coefficient of static friction of less than about 3.

23. The method of claim 21, wherein the coated orally ingestible substrate has a coefficient of dynamic friction of less than about 1.5.

24. The composition of claim 8, wherein the maltodextrin comprises 5-60% by weight of the film coating composition.

* * * * *